United States Patent [19]

Andrea

[11] Plant 4,215

[45] Feb. 14, 1978

[54] GERANIUM PLANT

[76] Inventor: Frank Andrea, 390 N. Franklin St., Holbrook, Mass. 02343

[21] Appl. No.: 776,908

[22] Filed: Mar. 11, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Clarence A. O'Brien; Harvey B. Jacobson

[57] ABSTRACT

A geranium of the Fiat type, characterized by its large trusses bearing large, double, pink florets.

1 Drawing Figure

The present discovery relates to a new and distinct geranium plant. The new and patentable characteristics thereof reside in its healthy growth, its continuous and exceptionally free-blooming habits, its large and double flowered truss, its large florets with double petalage and its distinctive color combination and unique foliage.

This geranium plant is a new and improved variety which has resulted from definite breeding programs and experiments carried on by me in my greenhouses at 390 No. Franklin St., Holbrook, Mass. My experiments covered the three year period from April, 1972 to April, 1975. The breeding experiments carried on by me were to produce new varieties of the "Fiat" (unpatented) type. The claimed geranium is the result of crossing the F. Andrea geranium plant patented by me Apr. 19, 1966, U.S. Plant Pat. No. 2,621, with an unnamed seedling, then crossing a seedling from the cross-breeding and back cross-breeding with the F. Andrea geranium. The claimed geranium plant is the result of one of these back-cross seedlings.

The drawing shows the plant and flower of a fully developed geranium of the new variety claimed.

My new variety has the following characteristics:

THE PLANT

Growth: This new variety is a very prolific bloomer. The florets are incurved with a variable number of petals, producing a double effect. The flower "truss" head is large, and the petals last longer and are identically associated with U.S. Plant Pat. No. 2,621 giving a large display. The growth is vigorous and compact and attains an average height of 12 to 18 inches as a pot plant.

Blooming habit: Very free and continuous bloomer in winter and summer, indoors or out. A plant in a 4 inch pot produces 2 to 3 trusses at one time.

Inflorescense: Large, globular to somewhat flattened, compact umbel or truss, measuring 4 to 6 inches at diameter.

Foliage:

*Quantity.*—Abundant

*Size.*—Not typical of Fiat, but large in size identical to U.S. Plant Pat. 2,621.

*Color.*—A dark green when well grown.

*Shape.*—Disc to cup shaped and undulate with deeply lobed edge.

*Texture.*—Firm, thick, waxy, upper surface smooth; lower surface moderately hairy with no distinct pubescense.

*Stem.*—Short, strong, freely branching to produce a compact, vigorous plant.

*Peduncle.*—Strong, slightly pubescent. Color slightly lighter than foliage.

THE FLOWER

Truss:

*Size.*—Large, up to 6 inches in diameter.

*Shape.*—Compact, a flattened globe as it opens.

*Number of florets.*—Variable average is 20 to 25.

*Lasting quality.*—Excellent. Blooms remain open 10 days to 2 weeks, longer if kept dry. Doubleness and waxy petals resist petal rot.

Bud:

*Size.*—Approximately 1 inch in diameter.

*Color.*—Lavender 61 (The Royal Horticultural Society Horticultural Color Chart).

*Form.*—Pointed.

Florets:

*Size.*—Approximately 1 inch in diameter.

*Petalage.*—Double, variable with 5 to 12 average.

*Color.*—Outer petal, Rhodamine pink 527 Horticultural Color Chart; 62A Royal Horticultural Society Color Chart. Interior petal, Rose Bengal 25/2 Horticultural Color Chart; 61D The Royal Horticultural Society Chart. Color very stable with age and does not fade.

*Texture.*—Very firm, waxy and glistening.

*Form.*—Petals are slightly serrated on the edge and overlap. When all the florets are open, the globular truss resembles a hydrangea.

*Lasting quality.*—Average florets last a week and the truss up to 10 days to 2 weeks.

*Behavior.*—The petals have a distinctly double appearance to the flower and make the plant give a distinctly double appearance with prolific habit.

Having thus disclosed my invention, I claim:

1. A new and distinct variety of geranium plant, substantially as shown and described, characterized by its healthy growth; its continuous and exceptionally free blooming habits; its large and double flowered truss; its large florets with double petalage and distinctive color combination.

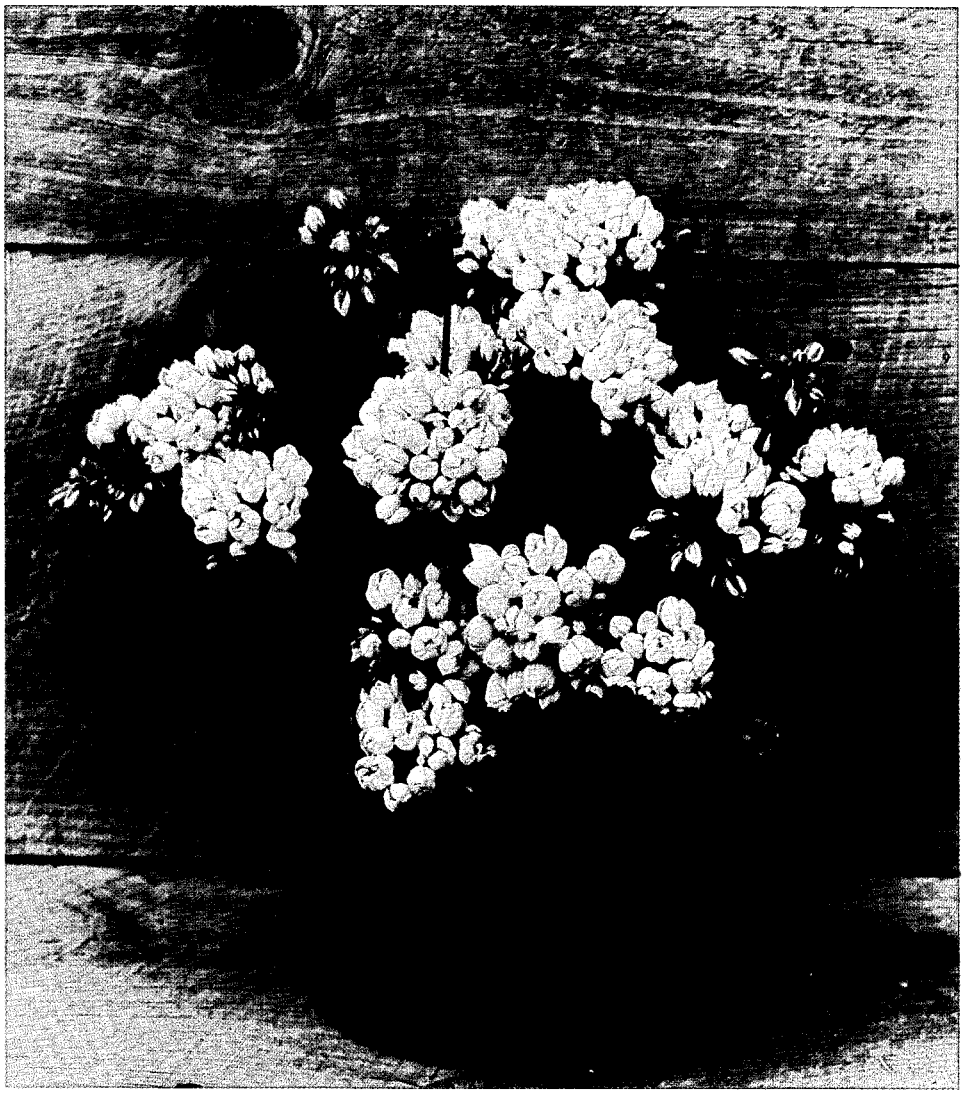

* * * * *